(12) United States Patent
Utsugida et al.

(10) Patent No.: US 10,478,105 B2
(45) Date of Patent: Nov. 19, 2019

(54) EXTRACORPOREAL CIRCULATION MANAGEMENT DEVICE AND EXTRACORPOREAL CIRCULATION DEVICE HAVING IT

(71) Applicant: TERUMO KABUSHIKI KAISHA, Tokyo (JP)

(72) Inventors: Tomoki Utsugida, Kanagawa (JP); Tomoaki Hashimoto, Kanagawa (JP); Tsuyoshi Hasegawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 254 days.

(21) Appl. No.: 15/629,898

(22) Filed: Jun. 22, 2017

(65) Prior Publication Data

US 2017/0281063 A1    Oct. 5, 2017

Related U.S. Application Data

(63) Continuation of application No. PCT/JP2015/074477, filed on Aug. 28, 2015.

(30) Foreign Application Priority Data

Dec. 25, 2014  (JP) .................................. 2014-262259

(51) Int. Cl.
*A61B 5/145* (2006.01)
*A61B 5/01* (2006.01)
(Continued)

(52) U.S. Cl.
CPC ............ *A61B 5/14542* (2013.01); *A61B 5/01* (2013.01); *A61M 1/32* (2013.01); *A61M 1/3666* (2013.01);
(Continued)

(58) Field of Classification Search
CPC .... A61B 5/01; A61B 5/14542; A61M 1/1698; A61M 1/3666; A61M 2205/3334; A61M 2205/52; A61M 2230/205
See application file for complete search history.

(56) References Cited

U.S. PATENT DOCUMENTS 5,810,759 A    9/1998   Merz

FOREIGN PATENT DOCUMENTS

| EP | 1721571 A1 | 11/2006 |
|---|---|---|
| JP | 2006122111 A | 5/2006 |

(Continued)

OTHER PUBLICATIONS

European Search and opinion Report, PCT/JP2015074477, dated May 11, 2018.

*Primary Examiner* — Leslie R Deak
(74) *Attorney, Agent, or Firm* — MacMillan, Sobanski & Todd, LLC

(57) ABSTRACT

An extracorporeal blood circulation management device having an oxygenator accurately determines oxygen consumption by the target person and oxygen delivery by the oxygenator. Oxygenation-related parameter values in the blood are determined at regular intervals. An in-body passing time (a cycle time for a particular volume of blood to pass from input sensors to output sensors) is determined. Parameter values separated by the in-body passing time are selected as comparison targets to evaluate oxygenation consumption of the target person. An oxygenator unit passing time is determined. Parameter values separated by the oxygenator unit passing time are selected as comparison targets to evaluate oxygenation delivery of the oxygenation unit.

15 Claims, 16 Drawing Sheets

(51) Int. Cl.
*A61M 1/32* (2006.01)
*A61M 1/36* (2006.01)
*A61M 1/16* (2006.01)

(52) U.S. Cl.
CPC ... *A61M 1/1698* (2013.01); *A61M 2205/3334* (2013.01); *A61M 2205/52* (2013.01); *A61M 2230/205* (2013.01)

(56) References Cited

FOREIGN PATENT DOCUMENTS

| WO | 2012013925 A2 | 2/2012 |
| WO | 2013128375 A1 | 9/2013 |

51 — OXYGEN SATURATION AND OXYGEN PARTIAL PRESSURE INFORMATION ACQUIRING UNIT (PROGRAM) (REFERS TO "TIMING DEVICE," "VENOUS-SIDE OXYGEN SATURATION MEASURING UNIT," "ARTERIAL-SIDE OXYGEN SATURATION MEASURING UNIT," "VENOUS-SIDE OXYGEN PARTIAL PRESSURE MEASURING UNIT," AND "ARTERIAL-SIDE OXYGEN PARTIAL PRESSURE MEASURING UNIT" AND STORES MEASUREMENT DATA OF EACH MEASURING UNIT OF EACH CLOCK TIME IN "OXYGEN SATURATION AND OXYGEN PARTIAL PRESSURE INFORMATION STORING UNIT")

52 — OXYGEN SATURATION AND OXYGEN PARTIAL PRESSURE INFORMATION STORING UNIT

53 — PAST DATA PRESENCE/ABSENCE CHECK PROCESSING UNIT (PROGRAM) (REFERS TO "FINAL IN-BODY BLOODSTREAM PASSING TIME STORING UNIT" AND "OXYGENATOR BLOODSTREAM PASSING TIME STORING UNIT" AND DETERMINES WHETHER OR NOT OXYGEN SATURATION DATA AND OXYGEN PARTIAL PRESSURE DATA OF CLOCK TIMES EARLIER THAN PRESENT BY "0.36 min" AND BY "0.065 min" ARE STORED IN "OXYGEN SATURATION AND OXYGEN PARTIAL PRESSURE INFORMATION STORING UNIT")

54 — FIRST PRESENT CLOCK TIME BIOLOGICAL INFORMATION EXTRACTION PROCESSING UNIT (PROGRAM) (REFERS TO "TIMING DEVICE" AND "OXYGEN SATURATION AND OXYGEN PARTIAL PRESSURE INFORMATION STORING UNIT" AND STORES VALUES OF SATURATION OF VENOUS OXYGEN (72%) AND PARTIAL PRESSURE OF VENOUS OXYGEN (40 mmHg) OF PRESENT CLOCK TIME IN "FIRST PRESENT CLOCK TIME BIOLOGICAL INFORMATION STORING UNIT")

55 — FIRST PRESENT CLOCK TIME BIOLOGICAL INFORMATION STORING UNIT (FOR EXAMPLE, VALUES OF SATURATION OF VENOUS OXYGEN (72%) AND PARTIAL PRESSURE OF VENOUS OXYGEN (40 mmHg) OF PRESENT CLOCK TIME)

56 — FIRST PAST CLOCK TIME BIOLOGICAL INFORMATION EXTRACTION PROCESSING UNIT (PROGRAM) (REFERS TO "TIMING DEVICE," "OXYGEN SATURATION AND OXYGEN PARTIAL PRESSURE INFORMATION STORING UNIT," AND "FINAL IN-BODY BLOODSTREAM PASSING TIME STORING UNIT" AND STORES VALUES OF SATURATION OF ARTERIAL OXYGEN (98%) AND PARTIAL PRESSURE OF ARTERIAL OXYGEN (132 mmHg) OF CLOCK TIME EARLIER THAN PRESENT CLOCK TIME BY FINAL IN-BODY BLOODSTREAM PASSING TIME (0.36 min)) IN "FIRST PAST CLOCK TIME BIOLOGICAL INFORMATION STORING UNIT"

FIG.13

| CLOCK TIME | | SATURATION OF ARTERIAL OXYGEN (%) | SATURATION OF VENOUS OXYGEN (%) | PARTIAL PRESSURE OF ARTERIAL OXYGEN (mmHg) | PARTIAL PRESSURE OF VENOUS OXYGEN (mmHg) |
|---|---|---|---|---|---|
| 1) 12:02:37.00 | | 99 | 71 | 130 | 40 |
| 2) 12:03:01.00 | (0.36 min BEFORE) | 97 | 72 | 132 | 41 |
| | ~ | ~ | ~ | ~ | ~ |
| 3) | | 98 | 73 | 131 | 40 |
| 4) | | 98 | 72 | 132 | 40 |
| 5) 12:03:36.35 | (0.065 min BEFORE) | 99 | 72 | 130 | 42 |
| | ~ | ~ | ~ | ~ | ~ |
| 6) | | 97 | 73 | 131 | 41 |
| 7) | | 98 | 71 | 130 | 42 |
| 8) 12:03:37.00 | (PRESENT) | 98 | 72 | 132 | 40 |

FIG.14

| CLOCK TIME | | SATURATION OF ARTERIAL OXYGEN (%) | SATURATION OF VENOUS OXYGEN (%) | PARTIAL PRESSURE OF ARTERIAL OXYGEN (mmHg) | PARTIAL PRESSURE OF VENOUS OXYGEN (mmHg) |
|---|---|---|---|---|---|
| 1) 12:02:37.00 | (BODY TEMPERATURE RISE) | 99 | 71 | 130 | 40 |
| 2) 12:03:01.00 | (0.36 min BEFORE) | 97 | 72 | 132 | 41 |
| 3) ~ | | ~ | ~ | ~ | ~ |
| 3) | | 98 | 73 | 131 | 40 |
| 4) | | 98 | 72 | 132 | 40 |
| 5) 12:03:36.35 | (0.065 min BEFORE) | 99 | 72 | 130 | 42 |
| ~ | | ~ | ~ | ~ | ~ |
| 6) | | 97 | 73 | 131 | 41 |
| 7) | | 98 | 65 | 130 | 28 |
| 8) 12:03:37.00 | | 98 | 63 | 132 | 30 |
| 9) ~ | | 91 | ~ | 118 | ~ |

FIG. 15

| | |
|---|---|
| 81 | VENOUS-SIDE OXYGEN SATURATION ADJUSTING UNIT (PROGRAM) (MEASURES VALUE OF VENOUS-SIDE OXYGEN SATURATION MEASURING UNIT AND DETERMINES WHETHER OR NOT VALUE OF OXYGEN SATURATION IS EQUAL TO OR LARGER THAN 70% AND, IF VALUE IS NOT EQUAL TO OR LARGER THAN 70%, OPERATES OXYGENATOR TO ADJUST VALUE TO 70% OR LARGER) |
| 82 | ARTERIAL-SIDE OXYGEN SATURATION ADJUSTING UNIT (PROGRAM) (DETERMINES WHETHER VALUE OF ARTERIAL-SIDE OXYGEN SATURATION MEASURING UNIT IS SMALLER THAN 90% AND, IF VALUE IS SMALLER THAN 90%, REFERS TO TIMING DEVICE AND WAITS FOR ONE MINUTE) |
| 83 | ARTERIAL-SIDE OXYGEN SATURATION ADJUSTING UNIT (PROGRAM) (OPERATES OXYGENATOR TO SET VALUE OF ARTERIAL-SIDE OXYGEN SATURATION MEASURING UNIT TO 100% AND STORE CORRESPONDING CLOCK TIME IN "START CLOCK TIME STORING UNIT" WITH REFERENCE TO TIMING DEVICE) |
| 84 | START CLOCK TIME STORING UNIT |
| 85 | IN-BODY BLOOD PASSING TIME INFORMATION GENERATING UNIT (PROGRAM) (DETERMINES WHETHER OR NOT VALUE OF VENOUS-SIDE OXYGEN SATURATION MEASURING UNIT IS EQUAL TO OR LARGER THAN 80% AND, WHEN VALUE IS EQUAL TO OR LARGER THAN 80%, CALCULATES TIME WITH REFERENCE TO TIMING DEVICE AND START CLOCK TIME STORING UNIT AND STORES THIS TIME IN IN-BODY BLOOD PASSING TIME STORING UNIT AS IN-BODY BLOOD PASSING TIME) |
| 86 | IN-BODY BLOOD PASSING TIME STORING UNIT |

EXTRACORPOREAL CIRCULATION MANAGEMENT DEVICE AND EXTRACORPOREAL CIRCULATION DEVICE HAVING IT

This application is a continuation of PCT Application No. PCT/JP2015/074477, filed Aug. 28, 2015, based on and claiming priority to Japanese application no. 2014-262259, filed Dec. 25, 2014, both of which are incorporated herein by reference in their entirety.

TECHNICAL FIELD

The present invention relates to an extracorporeal circulation management device that manages an extracorporeal circulation to supply blood to a patient and an extracorporeal circulation device having it, for example.

BACKGROUND ART

Conventionally, for example, percutaneous cardiopulmonary support (PCPS) is used as an extracorporeal circulation method. This percutaneous cardiopulmonary support is a method in which cardiopulmonary support is carried out through femoral artery and vein by a pump-oxygenator device (extracorporeal circulation device) in a closed circuit using a centrifugal pump and a membrane oxygenator in general. Therefore, when supply of blood to a patient is necessary during an operation or the like, an extracorporeal circulation device having a pump-oxygenator and so forth is used in order to extracorporeally circulate the blood of the patient. Furthermore, it has been known to monitor the amount of movement of oxygen and carbon dioxide in the blood that circulates by such an extracorporeal circulation device has also been made (for example, Japanese Laid-open Patent Application No. 2006-122111).

Meanwhile, such an extracorporeal circulation device has a venous-side tube that is for guiding blood of a patient from the patient to the oxygenator and couples a vein of the patient and the oxygenator. In addition, the extracorporeal circulation device also has an arterial-side tube that is for supplying blood of the oxygenator to the patient and couples the oxygenator to an artery of the patient. Furthermore, the oxygen consumption or the like of the patient who uses the extracorporeal circulation system is obtained based on information on the oxygen saturation, hemoglobin, and so forth of blood in these venous-side tube and arterial-side tube.

SUMMARY OF INVENTION

Technical Problem

Although the patient who uses the extracorporeal circulation device is continuously supplied with blood with a predetermined oxygen concentration from the oxygenator, the oxygen saturation or the like of this blood supplied from the oxygenator does not remain constant. For this reason, there is the following problem. Specifically, even when the oxygen saturation or the like of the blood in the venous-side tube after consumption of oxygen and the oxygen saturation or the like of the blood in the arterial-side tube are compared, the possibility is high that the oxygen saturation or the like of the blood in the arterial-side tube is different from that of the blood before oxygen consumption in the patient calculated from that of the venous-side tube as the comparison target, and it is impossible to obtain the correct oxygen consumption or the like of the patient.

Therefore, the present invention intends to provide an extracorporeal circulation management device by which the oxygen consumption or the like in a patient regarding blood supplied from an oxygenator or the like can be correctly determined, as well as an extracorporeal circulation system having the improved management device.

Technical Solution

In the present invention, the aforesaid object is achieved by an extracorporeal circulation management device characterized by storing a plurality of pieces of first state information (i.e., oxygenation-related parameter values) of blood supplied from an oxygenator unit that carries out gas exchange of blood to a target person with time-course information and storing also a plurality of pieces of second state information of blood introduced from the target person into the oxygenator unit with time-course information, having in-body passing time information that is information on a time until the blood supplied from the oxygenator unit to the target person is discharged from the target person, and selecting the first state information and the second state information as comparison targets from the plurality of pieces of first state information and the plurality of pieces of second state information based on the in-body passing time information when comparing any of the plurality of pieces of first state information and any of the plurality of pieces of second state information.

Accordingly, the first state information and the second state information as comparison targets are selected from the plurality of pieces of first state information and the plurality of pieces of second state information based on the in-body passing time information when any of the plurality of pieces of first state information and any of the plurality of pieces of second state information are compared. Because the first state information and the second state information that should be compared are selected based on the in-body passing time information as above, correct information on the oxygen consumption or the like of the target person can be obtained through the comparison between the state information of the blood introduced into the body and the state information when this blood is discharged. Furthermore, the oxygen consumption or the like in the patient regarding the blood supplied from the oxygenator unit can be correctly grasped.

Preferably, the extracorporeal circulation management device is characterized by having a configuration in which information on in-body oxygen consumption or the like of the target person is acquired through comparison of the first state information and the second state information.

Preferably, the extracorporeal circulation management device is characterized by having a configuration in which the in-body passing time information is corrected based on introduction part information of the blood introduced from the oxygenator unit into the target person and discharge part information of discharge of the blood from the target person.

Accordingly, the in-body passing time information is corrected based on the introduction part information of the blood and the discharge part information of discharge of the blood from the target person. The in-body passing time (i.e., the time of passing of blood in the body of the target person) differs depending on the introduction part information and the discharge part information that are the sites at which cannulas are disposed, for example. Regarding this respect, correction is carried out based on the introduction part information and the discharge part information that are sites or the like of the target person in the configuration. This provides a configuration in which more accurate estimates of in-body passing time information can be generated. Therefore, the oxygen consumption or the like in the patient regarding the blood supplied from the oxygenator unit can be determined more accurately.

Preferably, the extracorporeal circulation management device is characterized by measuring the first state information and the second state information and generating the in-body passing time information based on change information of the first state information and the second state information.

According to the illustrated embodiment of the invention, the first state information and the second state information are actually acquired by measurement and the time is identified based on the change information between them. Thus, highly accurate in-body passing time information can be generated and thereby the oxygen consumption or the like in the patient regarding the blood supplied from the oxygenator unit can be determined more correctly.

Preferably, the extracorporeal circulation management device is characterized by having oxygenator unit passing time information that is a time until blood is supplied from the target person to the oxygenator unit and the oxygenator unit carries out gas exchange and discharges the blood, and selecting the first state information and the second state information as comparison targets from the plurality of pieces of first state information and the plurality of pieces of second state information based on the oxygenator unit passing time information when comparing any of the plurality of pieces of first state information and any of the plurality of pieces of second state information.

According to the illustrated embodiment, the first state information and the second state information as comparison targets are selected from the plurality of pieces of first state information and the plurality of pieces of second state information based on the oxygenator unit passing time information when any of the plurality of pieces of first state information and any of the plurality of pieces of second state information are compared. Therefore, because the first state information and the second state information that should be compared are selected based on the oxygenator unit passing time information as above, the oxygen delivery, which is the capability of adding oxygen by the oxygenator unit, can be correctly estimated through the comparison between the state information of the blood introduced into the oxygenator unit and the state information when this blood is discharged. Furthermore, pieces of information of the oxygen delivery and the oxygen consumption can be separately acquired. Thus, when an abnormality exists in the numerical value or the like of either one of the oxygen delivery and the oxygen consumption, an abnormal condition can be rapidly identified.

Preferably, the extracorporeal circulation management device is characterized by being capable of rapidly identifying which of the oxygen delivery or the like and the oxygen consumption or the like is abnormal when an abnormality exists in a numerical value or the like of either one of the oxygen delivery or the like and the oxygen consumption or the like by separately acquiring the information on the oxygen consumption or the like and the information on the oxygen delivery or the like.

Preferably, an extracorporeal circulation device of the invention has the oxygenator unit and a tube part for providing blood of the oxygenator unit to the target person and the first state information and the second state information are state information relating to blood in the tube part.

Advantageous Effect

As described above, according to the present invention, there is an advantage that it is possible to provide an extracorporeal circulation management device by which the oxygen consumption or the like in a patient regarding blood supplied from an oxygenator or the like can be accurately determined.

BRIEF DESCRIPTION OF DRAWINGS

FIG. 6 is a schematic block diagram showing the main configuration of a third various-kinds-of-information storing unit.

FIG. 13 is a schematic explanatory diagram showing each piece of measurement data stored in an oxygen saturation and oxygen partial pressure information storing unit.

FIG. 14 is a schematic explanatory diagram showing the relationship between the oxygen consumption and the oxygen delivery in association with a rise in the body temperature.

FIG. 15 is a schematic block diagram showing the main configuration of an extracorporeal circulation device according to a second embodiment of the present invention.

DETAILED DESCRIPTION OF PREFERRED EMBODIMENTS

Preferred embodiments of this invention will be described in detail below with reference to the accompanying drawings and so forth. Note that the embodiments to be described below are preferred concrete examples of the present invention and therefore are given various qualifications that are technically preferable. However, the scope of the present invention is not limited to these aspects unless there is a particular description of limiting the present invention in the following explanation.

First Embodiment

Figure 1:
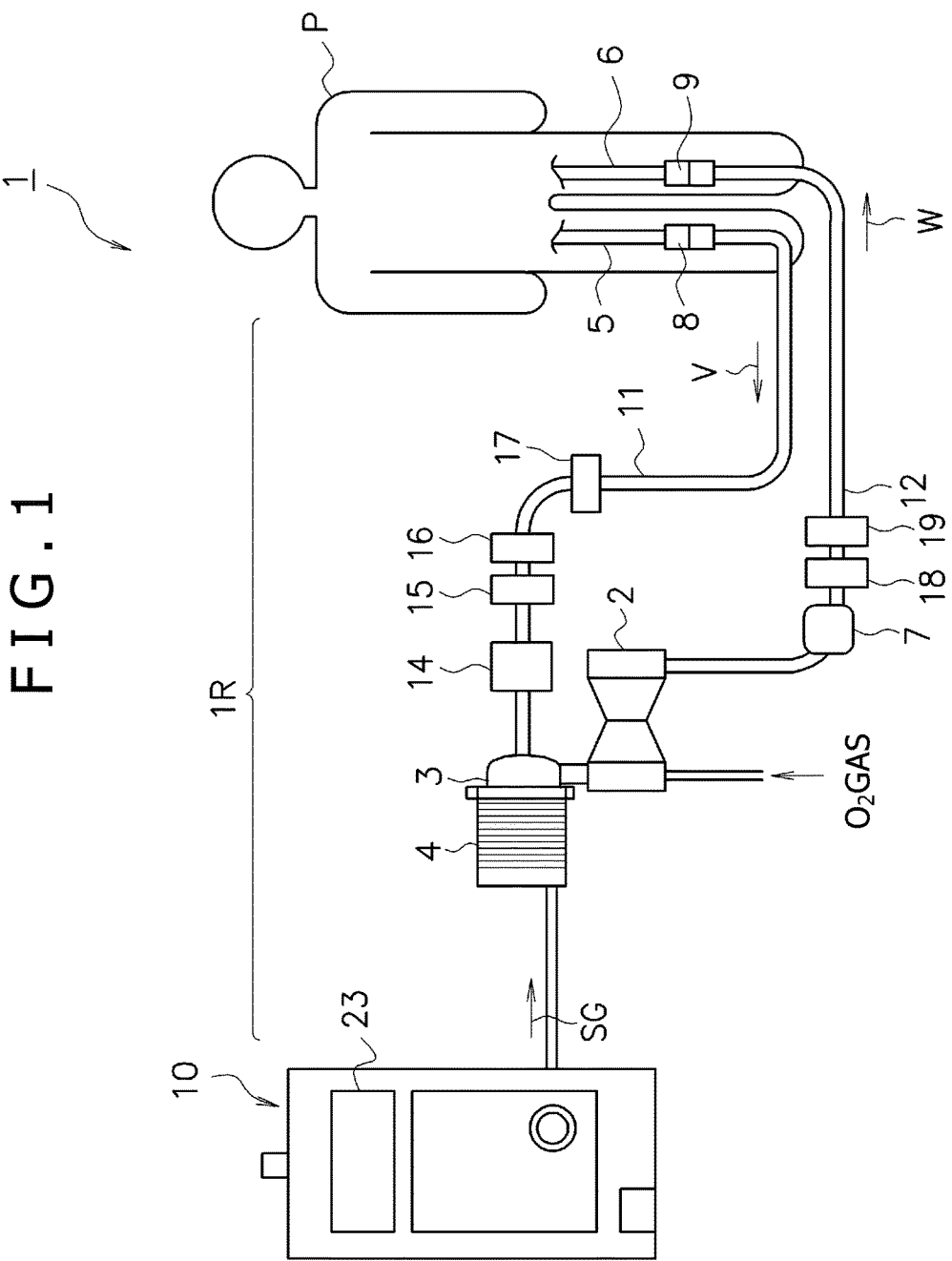
FIG. 1 is a schematic diagram showing the main configuration of an extracorporeal circulation device according to a first embodiment of the present invention.

FIG. 1 is a schematic diagram showing the main configuration of an extracorporeal circulation system 1 according to a first embodiment of the present invention. The extracorporeal circulation system 1 shown in FIG. 1 is a device that carries out an extracorporeal circulation of blood of, e.g., a patient P that is a target person shown in FIG. 1. In this "extracorporeal circulation," "cardiopulmonary bypass" and "extracorporeal membrane oxygenation" are included.

The "cardiopulmonary bypass" is carrying out circulation operation of blood and gas exchange operation (oxygen addition and/or carbon dioxide removal) for this blood by this extracorporeal circulation system 1 in the case in which the blood does not circulate to the heart of the patient (subject) P as the application target of the extracorporeal circulation system 1 and thus gas exchange cannot be carried out in the body of the patient P. Furthermore, the "extracorporeal membrane oxygenation" is carrying out support of circulation operation of blood also by the extracorporeal circulation system 1 in the case in which the blood circulates to the heart of the patient (subject) P as the application target of the extracorporeal circulation system 1 and gas exchange can be carried out in the lung of the patient P. Some devices have a function of carrying out gas exchange operation for blood.

The extracorporeal circulation system 1 shown in FIG. 1 according to the present embodiment is used in the case of performing a cardiac surgery operation of the patient P or the like, for example. Specifically, an "oxygenator extracorporeal blood circulation" is carried out in which a centrifugal pump 3 of the extracorporeal circulation system 1 is actuated to remove blood from a vein (great vein) of the patient P and gas exchange in the blood is carried out to add oxygen to the blood by, e.g., an oxygenator 2 that is an oxygenator unit and thereafter this blood is returned to an artery (great artery) of the patient P again. That is, the extracorporeal circulation system 1 is a device that substitutes for the heart and the lung.

Furthermore, the extracorporeal circulation system 1 has the following configuration. Specifically, as shown in FIG. 1, the extracorporeal circulation system 1 has a "circulation circuit 1R" that circulates blood. The circulation circuit 1R has the "oxygenator 2," the "centrifugal pump 3," a "drive motor 4," a "venous-side cannula (blood-removal-side cannula) 5," an "arterial-side cannula (blood-sending-side cannula) 6," and, e.g., a controller 10 that is an extracorporeal circulation management device. Note that the centrifugal pump 3 is referred to also as a blood pump and a pump other than the centrifugal-type pump can also be used.

Furthermore, the venous-side cannula (blood-removal-side cannula) 5 in FIG. 1 is inserted from the femoral vein and the distal of the venous-side cannula 5 is indwelled in the right atrium. The arterial-side cannula (blood-sending-side cannula) 6 is inserted from the femoral artery through a connector 9 in FIG. 1. The venous-side cannula 5 is connected to the centrifugal pump 3 via a connector 8 by using, e.g., a blood removal tube 11 that is a tube part. The blood removal tube (referred to also as "blood removal line") 11 is a conduit that sends blood. A configuration is made in which, when the drive motor 4 causes the centrifugal pump 3 to be operated based on a command SG of the controller 10, the centrifugal pump 3 returns the blood that is removed from the blood removal tube 11 and is made to pass through the oxygenator 2 to the patient P through, e.g., a blood sending tube 12 (referred to also as "liquid sending line") that is a tube part.

The oxygenator 2 is disposed between the centrifugal pump 3 and the blood sending tube 12. The oxygenator 2 introduces an oxygen gas as shown in FIG. 1 and carries out gas exchange operation (oxygen addition and/or carbon dioxide removal) for this blood. The oxygenator 2 is a membrane oxygenator, for example, and particularly preferably a hollow fiber membrane oxygenator is used. The blood sending tube 12 is a conduit that connects the oxygenator 2 and the arterial-side cannula 6. The blood removal tube 11 and the blood sending tube 12 are conduits made of a synthetic resin having high transparency and flexibility, such as a vinyl chloride resin or silicone rubber, for example and have an outer diameter of approximately 14 mm and an inner diameter of approximately 10 mm. These tubes are made to contain, besides a plasticizer, approximately 1 to 2 wt % of a benzotriazole-based ultraviolet absorbers (UVA: hindered amine-based light stabilizer), which is excellent in the initial color tone and has high ultraviolet absorption capability. Thereby, ultraviolet deterioration due to a fluorescent light or the like in a room is prevented and the safety is improved. In the blood removal tube 11, blood flows in a V-direction. In the blood sending tube 12, blood flows in a W-direction.

Furthermore, in the extracorporeal circulation system 1, on its blood sending tube 12, an arterial-side oxygen partial pressure measuring unit 18 that measures the partial pressure of arterial oxygen (mmHg) regarding the blood in the blood sending tube 12 is disposed as shown in FIG. 1. This oxygen partial pressure is an index that indicates the oxygenation capability of the blood.

Moreover, on the blood sending tube 12, an arterial-side oxygen saturation measuring unit 19 that measures the oxygen saturation (%) in the blood in the blood sending tube 12 is disposed. This oxygen saturation is an index that indicates the ratio of binding to hemoglobin in the blood. In addition, for the blood sending tube 12, a clamp 7 for blocking blood from being sent to the patient P in an abnormal state when a flow rate abnormality or the like occurs in the blood in the blood sending tube 12 is formed. This provides a configuration in which an operator can urgently occlude the blood sending tube 12 by using this clamp 7 (tube occluding device).

Meanwhile, on the blood removal tube 11 in FIG. 1, a venous-side oxygen partial pressure measuring unit 15 that measures the partial pressure of venous oxygen (mmHg) regarding the blood in the blood removal tube 11 is disposed. In addition, a venous-side oxygen saturation measuring unit 16 that measures the oxygen saturation (%) in the blood in the blood removal tube 11 is disposed. Furthermore, on the blood removal tube 11, a hemoglobin measuring unit 17 that detects the value of hemoglobin of the blood in the blood removal tube 11 is disposed. Moreover, the extracorporeal circulation system 1 has a "flow rate sensor 14" on the blood removal tube 11. This flow rate sensor 14 is a sensor that measures the flow rate value of the blood that passes through the blood removal tube 11 and senses also an abnormality in the flow rate value.

Incidentally, the controller 10 or the like of the extracorporeal circulation system 1 shown in FIG. 1 may be comprised of a computer. The computer has a central processing unit (CPU), a random access memory (RAM), a read only memory (ROM), and so forth, which are not diagrammatically represented, and they are connected through a bus.

Figure 2:
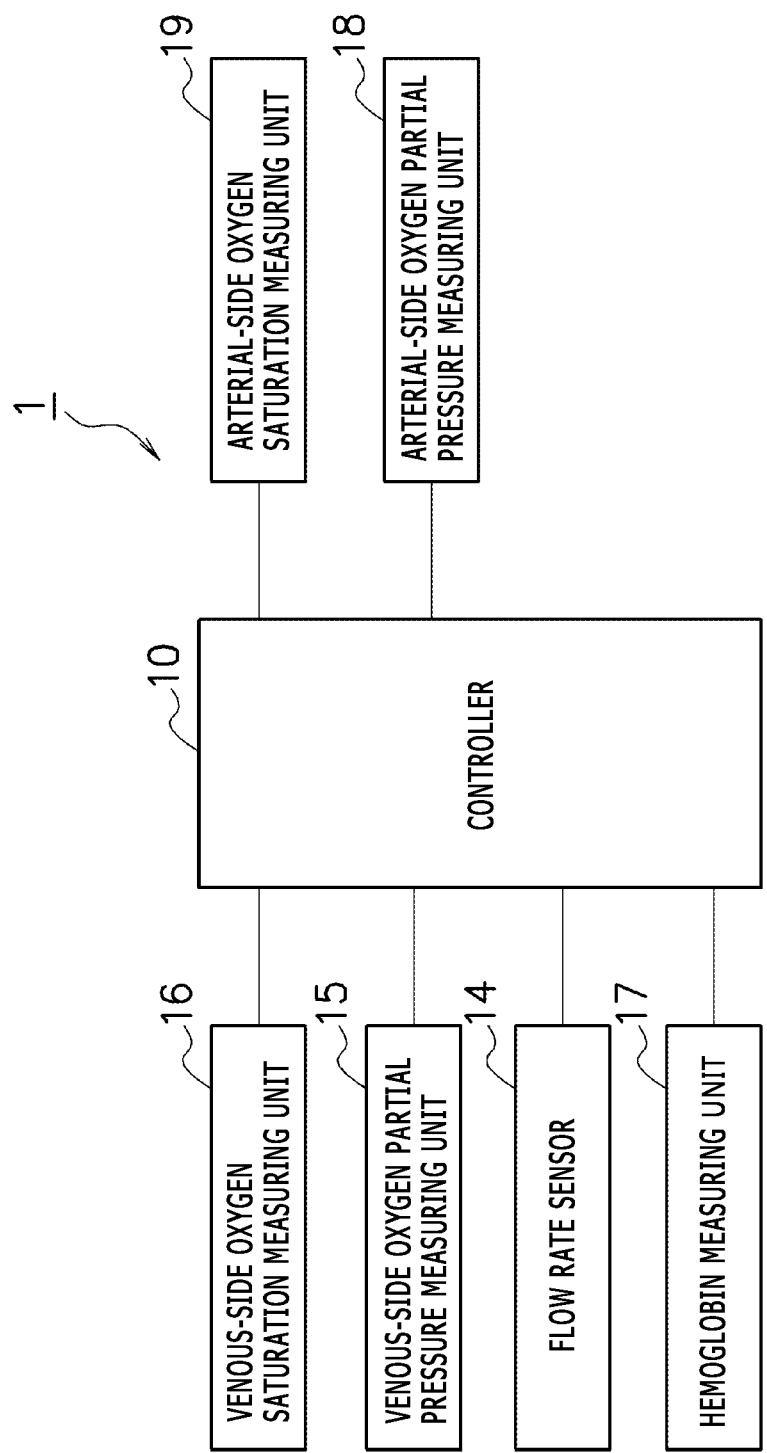
FIG. 2 is a schematic diagram showing the relationship between a controller of the extracorporeal circulation device of FIG. 1 and respective measuring units and so forth.

FIG. 2 is a schematic diagram showing the relationship between the controller 10 of the extracorporeal circulation system 1 of FIG. 1 and the respective measuring units and so forth. The controller 10 shown in FIG. 2 is communicably connected to the venous-side oxygen saturation measuring unit 16, the venous-side oxygen partial pressure measuring unit 15, the flow rate sensor 14, the hemoglobin measuring unit 17, the arterial-side oxygen saturation measuring unit 19, and the arterial-side oxygen partial pressure measuring unit 18 shown in FIG. 1. This connection may be not only a wired communication but also wireless communication. In the case of a wired communication, it is preferable to make the communication based on Recommended Standard (RS) 232C, which is robust against electromagnetic noise.

Figure 3:
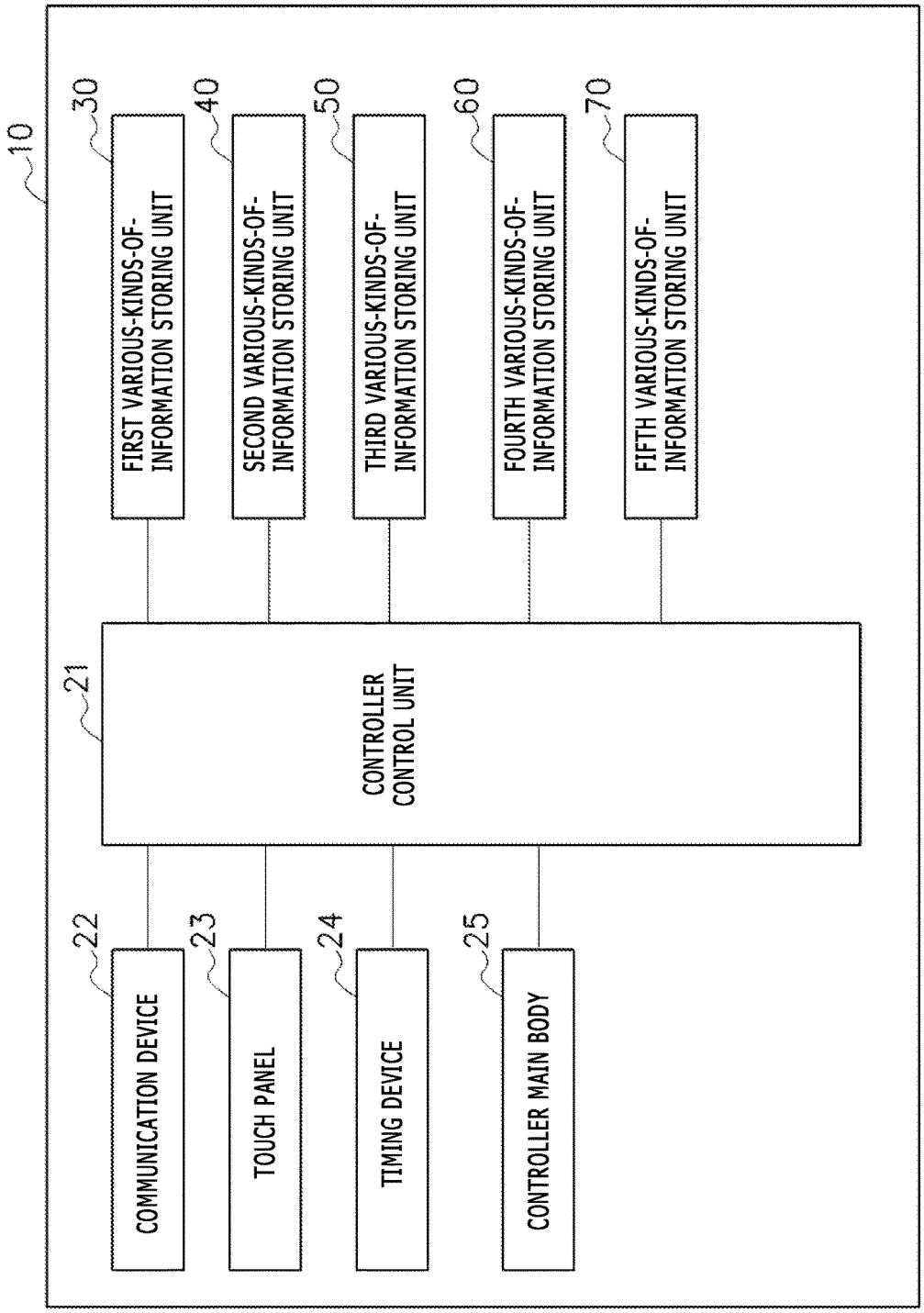
FIG. 3 is a schematic block diagram showing the main configuration of the controller in FIG. 1.

FIG. 3 is a schematic block diagram showing the main configuration of the controller 10 in FIG. 1. As shown in FIG. 3, the controller 10 has a "controller control unit 21." The controller control unit 21 has a configuration capable of controlling a communication device 22 for communication with the drive motor 4, the venous-side oxygen partial pressure measuring unit 15, and so forth shown in FIG. 1 and a "touch panel 23" that displays various kinds of information and allows input of various kinds of information and is formed of a color liquid crystal, organic electroluminescence (EL), or the like. Furthermore, the controller 10 also controls a timing device 24 that generates clock time information and a controller main body 25.

Moreover, the controller control unit 21 controls a "first various-kinds-of-information storing unit 30," a "second various-kinds-of-information storing unit 40," a "third various-kinds-of-information storing unit 50," a "fourth various-kinds-of-information storing unit 60," and a "fifth various-kinds-of-information storing unit 70" shown in FIG. 3. FIG. 4 to FIG. 8 are schematic block diagrams showing the main configurations of the "first various-kinds-of-information storing unit 30," the "second various-kinds-of-information storing unit 40," the "third various-kinds-of-information storing unit 50," the "fourth various-kinds-of-information storing unit 60," and the "fifth various-kinds-of-information storing unit 70," respectively. The contents of them will be described later.

FIG. 9 to FIG. 12 are schematic flowcharts showing main operation examples and so forth of the extracorporeal circulation device 1 of FIG. 1. In the following, description will be made along these flowcharts and the configurations and so forth of FIG. 1 to FIG. 8 and so forth will also be described. If an abnormality or the like occurs in the oxygen consumption (mL/minute) of the patient P who uses the extracorporeal circulation system 1 of the present embodiment, it is necessary to rapidly respond to the abnormality or the like. Thus, a configuration in which the oxygen consumption (mL/minute) of the patient P can be correctly determined is made. In addition, a configuration is made in which data of the oxygen delivery (mL/minute) of the oxygenator 2 can also be correctly determined in order to rapidly detect occlusion or the like of the oxygenator 2 in FIG. 1.

Figure 9:
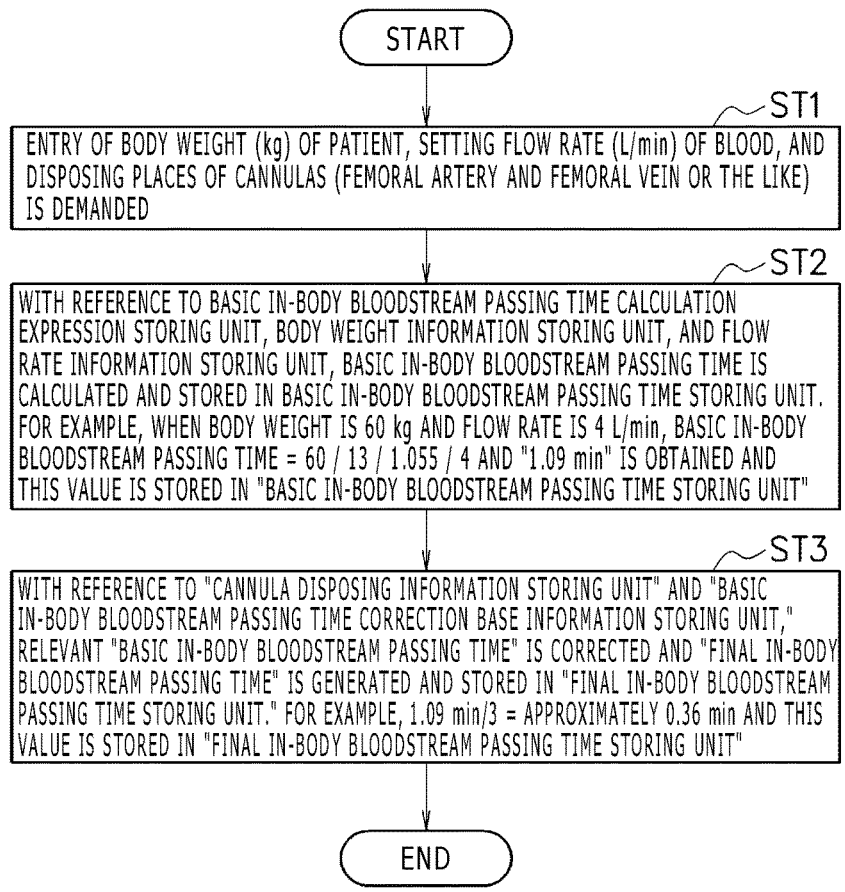
FIG. 9 is a schematic flowchart showing a calculation process for obtaining a final in-body bloodstream passing time.

Before data of the oxygen consumption of the patient P in FIG. 1 is acquired, basic data necessary for obtaining this oxygen consumption data is acquired. FIG. 9 is a schematic flowchart showing a calculation process for obtaining, e.g., a "final in-body bloodstream passing time" that is in-body passing time information. Specifically, this final in-body bloodstream passing time represents the amount of time that passes from the time when blood is introduced from the arterial-side cannula 6 in FIG. 1 and circulates (passes) in the body of the patient P until it is discharged from the venous-side cannula 5.

First, in a step ST (hereinafter, represented as "ST") 1 in FIG. 9, a data entry screen to demand an entry of the body weight (kg) of the patient P, the setting flow rate (L/minute) of blood of the extracorporeal circulation system 1, and the disposing places of the venous-side cannula 5 and the arterial-side cannula 6 is displayed on the touch panel 23 of the controller 10 in FIG. 1. To this screen on the touch panel 23, an operator (healthcare worker or the like) of the extracorporeal circulation system 1 enters the body weight of the patient P, e.g., 60 kg, and 4 L/minute as the flow rate. Furthermore, in the present embodiment, the disposing places of the arterial-side cannula 6 and the venous-side cannula 5 are the "femoral artery" and the "femoral vein" as shown in FIG. 1. Thus, they are entered. Note that the femoral artery as the disposing place of the arterial-side cannula 6 is one example of "introduction part information" and the femoral vein as the disposing place of the venous-side cannula 5 is one example of "discharge part information."

Figure 4:
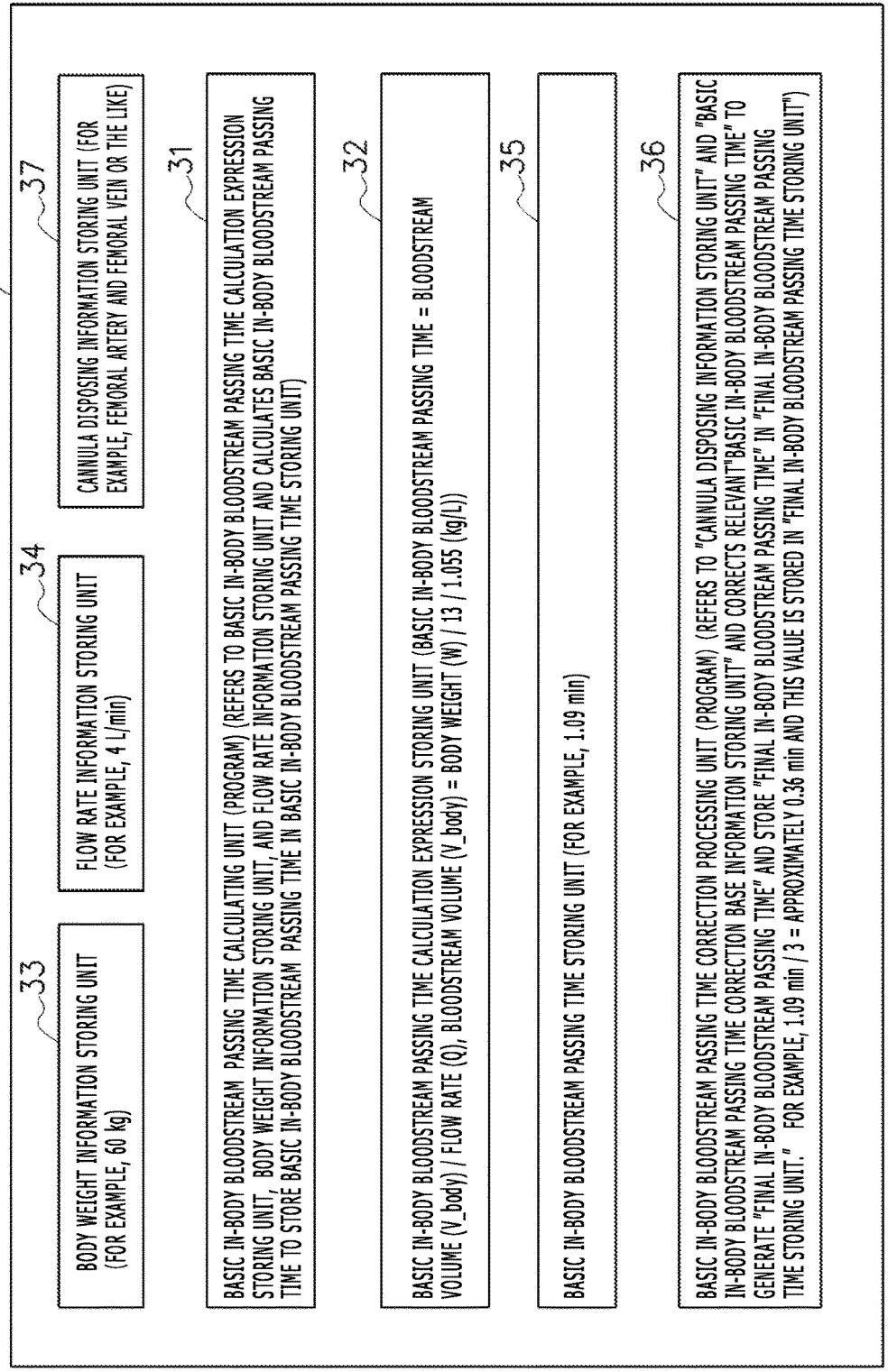
FIG. 4 is a schematic block diagram showing the main configuration of a first various-kinds-of-information storing unit.

In this case, the controller 10 stores "body weight 60 kg" in a "body weight information storing unit 33" in FIG. 4 and stores "4 mL/minute" in a "flow rate information storing unit 34." In addition, the controller 10 stores "femoral artery and femoral vein" in a "cannula disposing information storing unit 37."

Subsequently, the calculation process proceeds to ST2. In ST2, a "basic in-body bloodstream passing time calculating unit (program) 31" in FIG. 4 operates and refers to a "basic in-body bloodstream passing time calculation expression storing unit 32" in FIG. 4. The following expression is stored in the basic in-body bloodstream passing time calculation expression storing unit 32. Specifically, the expression is "basic in-body bloodstream passing time=bloodstream volume (V_body)/flow rate (Q), bloodstream volume (V_body) =body weight (W)/13/1.055 (kg/L)." Here, "1/13" represents that the bloodstream volume (amount) per body weight for a typical person is approximately 1/13 of the body weight, and "1.055 (kg/L)" represents the specific gravity of blood. Furthermore, this expression indicates that the "basic in-body bloodstream passing time," which is the basic time of the passing of blood in the body of the patient P, is defined by "bloodstream volume (V_body)/flow rate (Q)."

Furthermore, in ST2, with reference to the basic in-body bloodstream passing time calculation expression storing unit 32, the body weight information storing unit 33, and the flow rate information storing unit 34, pieces of data of them are substituted into the basic in-body bloodstream passing time calculation expression to calculate the "basic in-body bloodstream passing time." In the present embodiment, for example, when the body weight is 60 kg and the flow rate is 4 L/minute, the basic in-body bloodstream passing time=60/13/1.055/4 and "1.09 minutes" is obtained. Then, in ST2, this 1.09 minutes is stored in a "basic in-body bloodstream passing time storing unit 35." This basic in-body bloodstream passing time is one example of the in-body passing time information. In the present embodiment, this "1.09 minutes" is the basic information on the time of the passing of blood in the body of the patient P. However, even as the time of the passing of blood in the body of the same patient P, the time changes depending on the sites (i.e., entry and exit points) through which the blood passes. Thus, the basic in-body bloodstream passing time is corrected in the next step.

Figure 5:
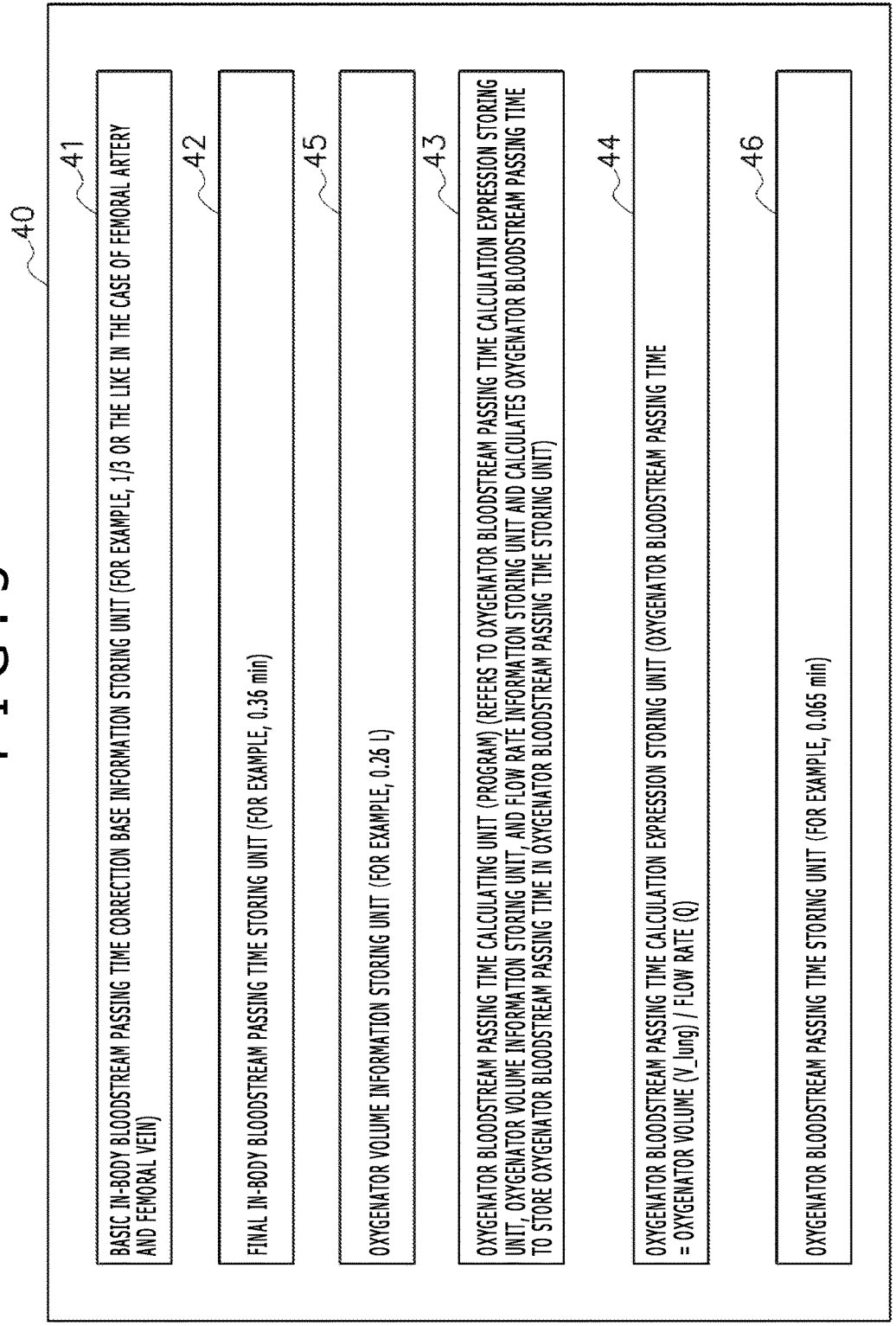
FIG. 5 is a schematic block diagram showing the main configuration of a second various-kinds-of-information storing unit.
Figure 7:
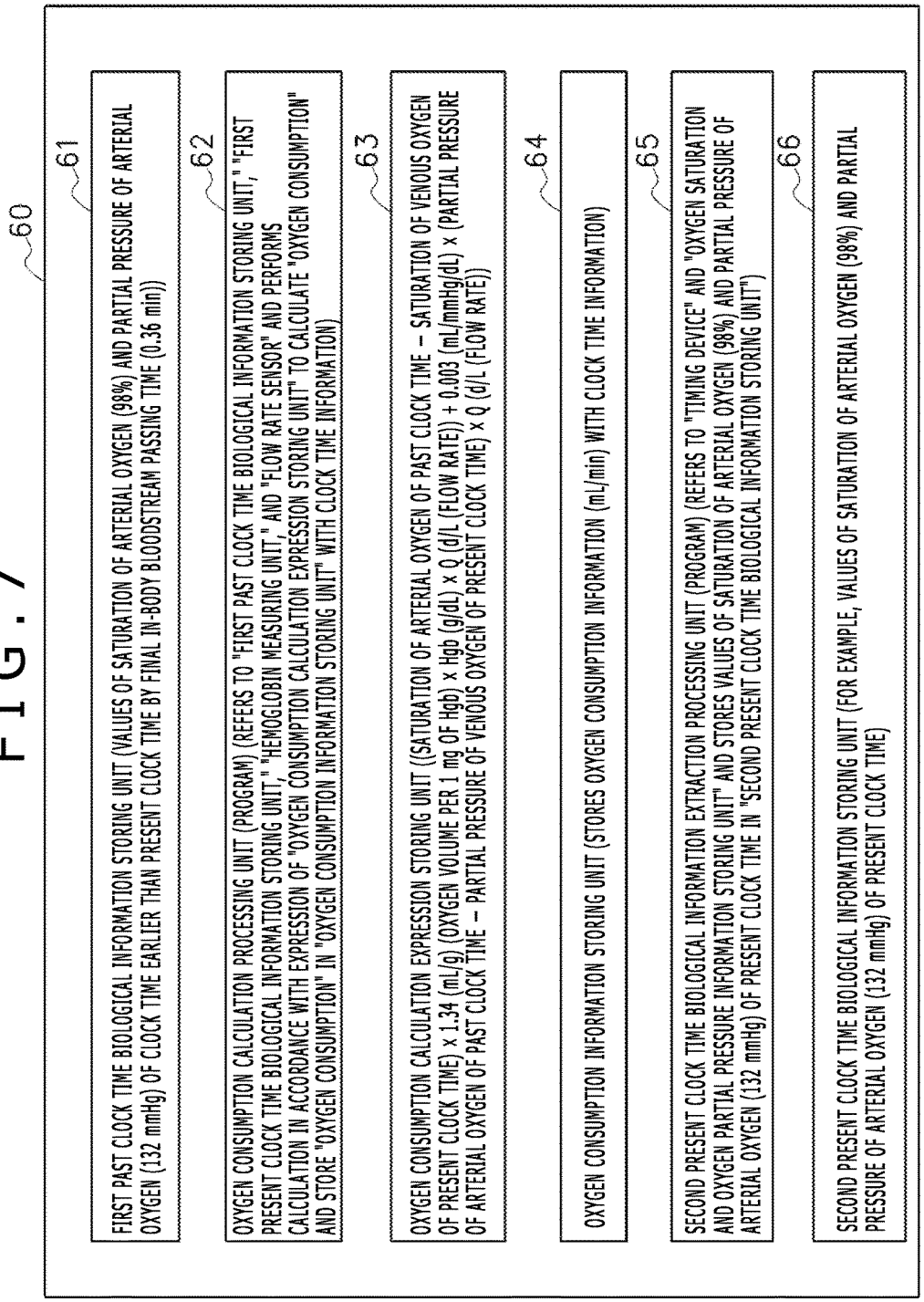
FIG. 7 is a schematic block diagram showing the main configuration of a fourth various-kinds-of-information storing unit.

In ST3, a "basic in-body bloodstream passing time correction processing unit (program) 36" in FIG. 4 operates and refers to the cannula disposing information storing unit 37 in FIG. 4 and a "basic in-body bloodstream passing time correction base information storing unit 41" in FIG. 5. In the basic in-body bloodstream passing time correction base information storing unit 41, the disposing places of cannulas and correction information of the basic in-body bloodstream passing time are associated and stored. For example, in the case of "femoral artery and femoral vein," the correction information is stored as "⅓."

Therefore, in ST3, the basic in-body bloodstream passing time correction base information is identified based on cannula disposing information and the data of the "basic in-body bloodstream passing time storing unit 35" in FIG. 4, e.g. 1.09 minutes, is corrected. In the present embodiment, 1.09 minutes/3=approximately 0.36 minute is obtained and this value is stored in a "final in-body bloodstream passing time storing unit 42" in FIG. 5 as the "final in-body bloodstream passing time."

By correcting the in-body bloodstream passing time based on the disposing places of cannulas in this manner, the more correct in-body bloodstream passing time can be generated.

Figure 10:
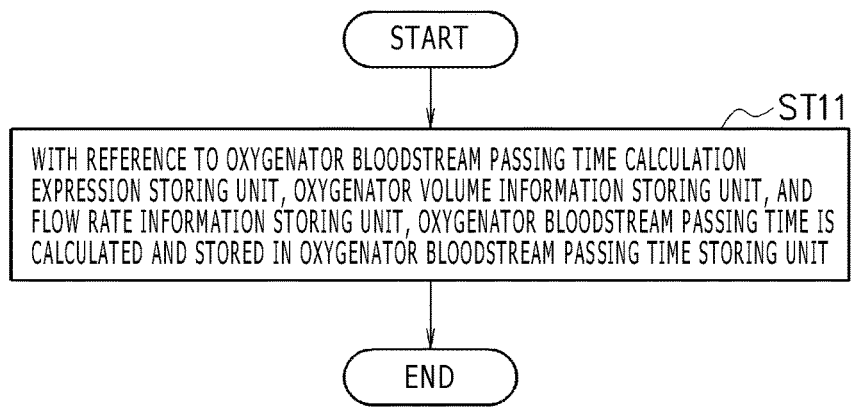
FIG. 10 is a schematic flowchart showing a calculation process for obtaining an oxygenator bloodstream passing time.

Subsequently, before oxygen delivery (mL/minute) data of the oxygenator 2 in FIG. 1 is determined, basic data necessary for obtaining this oxygen delivery data is acquired. FIG. 10 is a schematic flowchart showing a calculation process for obtaining an "oxygenator bloodstream passing time." Specifically, this oxygenator bloodstream passing time represents the time until blood introduced from the blood removal tube 11 in FIG. 1 into the oxygenator 2 is discharged from the oxygenator 2.

In ST11 in FIG. 10, an "oxygenator bloodstream passing time calculating unit (program) 43" in FIG. 5 operates and refers to an "oxygenator bloodstream passing time calculation expression storing unit 44" in FIG. 5. The following expression is stored in the oxygenator bloodstream passing time calculation expression storing unit 44. Specifically, the expression is "oxygenator bloodstream passing time=oxygenator volume (V_lung)/flow rate (Q)." This indicates that the "oxygenator bloodstream passing time," which is the time of the discharge of the blood introduced from the blood removal tube 11 into the oxygenator 2 to the blood sending tube 12, is obtained by "oxygenator volume (V_lung)/flow rate (Q)."

Furthermore, in an "oxygenator volume information storing unit 45" in FIG. 5, information on the oxygenator volume of the oxygenator 2, e.g. "0.26 L," is stored. Therefore, in ST11, with reference to "0.26 L" of the oxygenator volume information storing unit 45 and "4 L/minute" of the flow rate information storing unit 34 in FIG. 4, the numerical values of them are substituted into the expression of the oxygenator bloodstream passing time calculation expression storing unit 44.

In this case, oxygenator bloodstream passing time=0.26/4=0.065 minute (3.9 seconds). This 0.065 minute is stored as the oxygenator bloodstream passing time in an "oxygenator bloodstream passing time storing unit 46" in FIG. 5. In the present embodiment, this "0.065 minute" is the time of the passing of blood in the oxygenator 2. This oxygenator bloodstream passing time is one example of "oxygenator unit passing time information."

Figure 11:
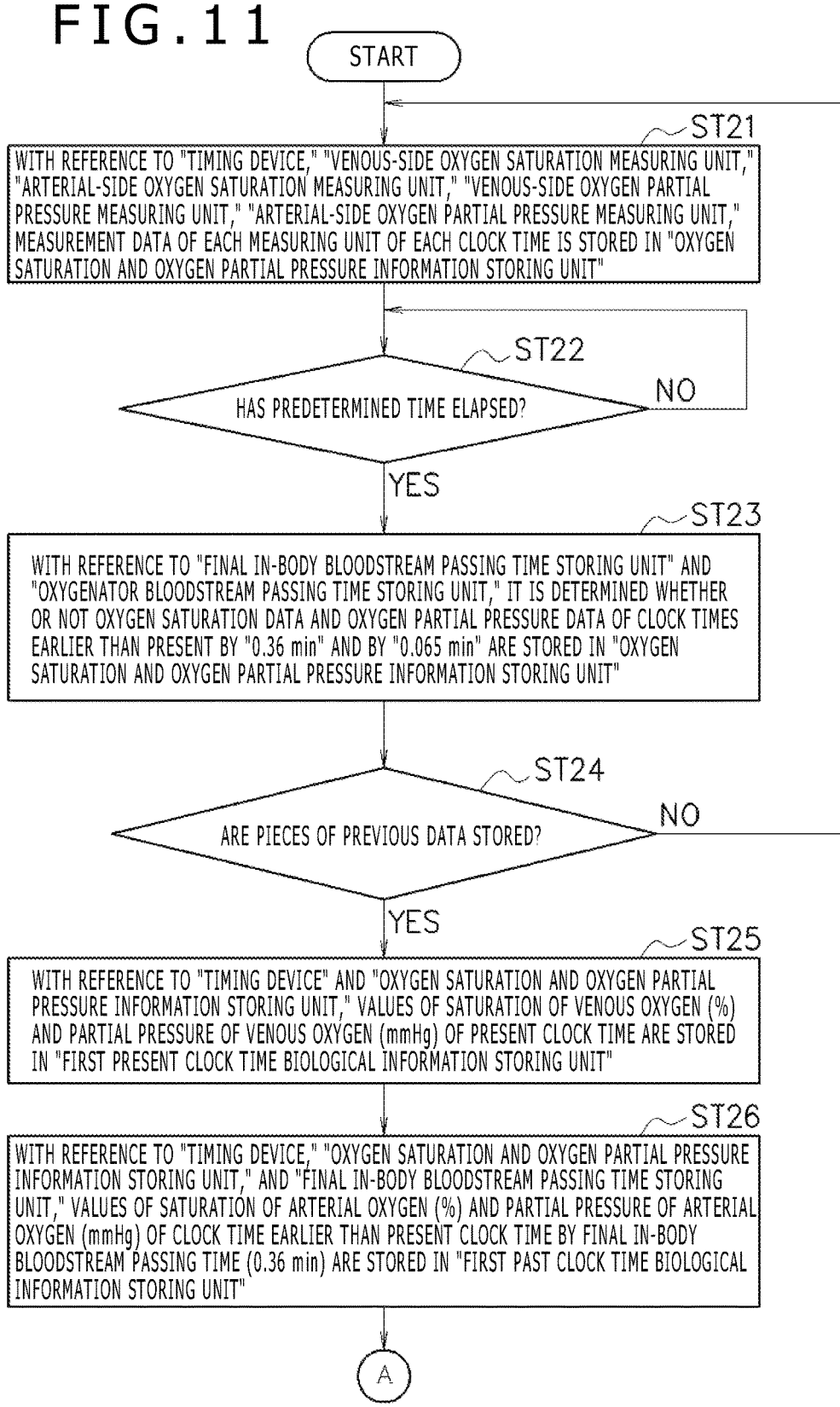
FIG. 11 is a schematic flowchart for explaining an acquisition process of oxygen consumption data of a patient and oxygen consumption data of an oxygenator.
Figure 12:
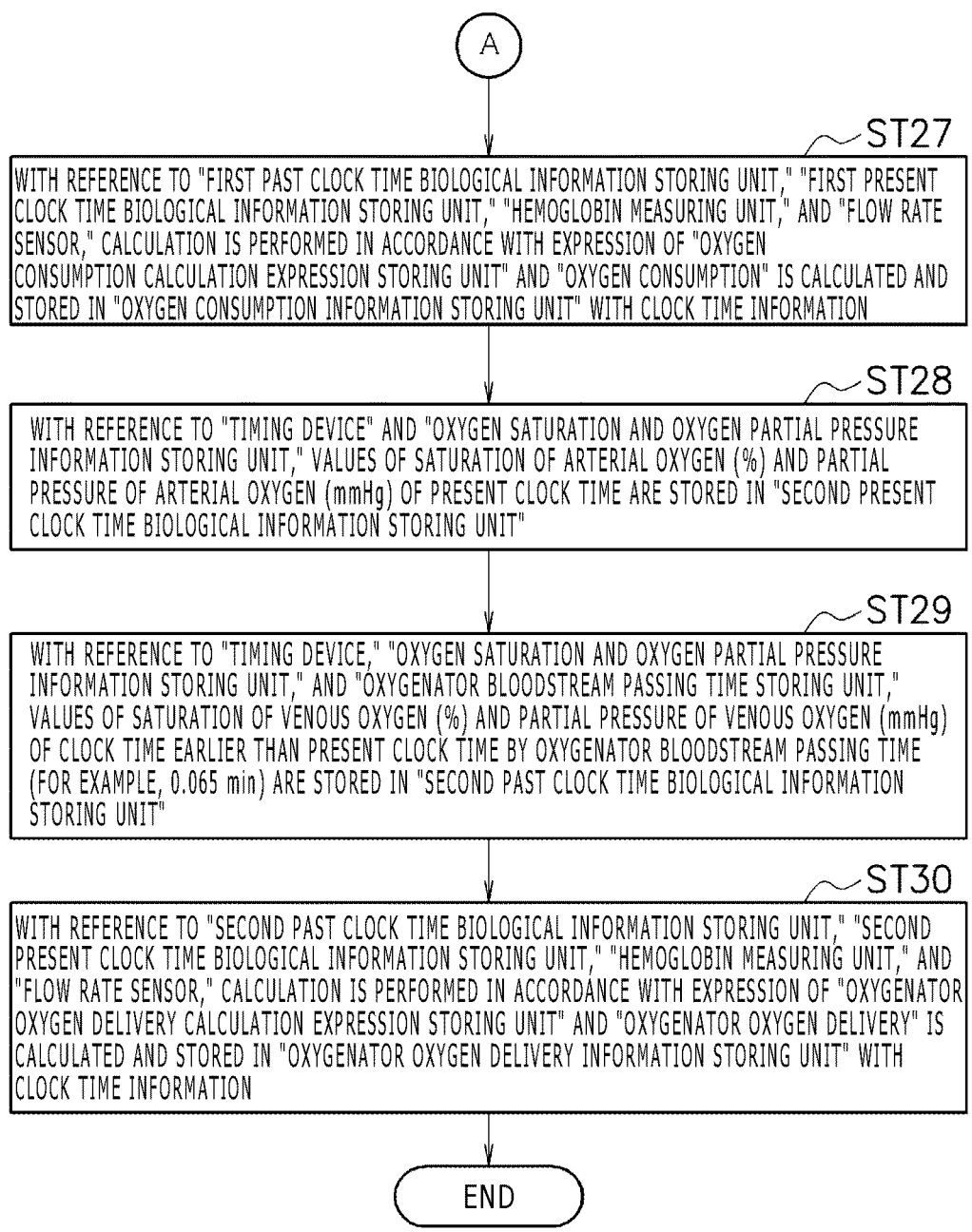
FIG. 12 is another schematic flowchart for explaining the acquisition process of the oxygen consumption data of the patient and the oxygen consumption data of the oxygenator.

Through the above, the acquisition of the basic data for correctly calculating the data of the oxygen consumption (mL/minute) of the patient P and the oxygen delivery (mL/minute) of the oxygenator 2 is accomplished. Subsequently, by using flowcharts of FIG. 11 and FIG. 12, an acquisition process of actually acquiring oxygen consumption data of the patient P and oxygen consumption data of the oxygenator 2 will be described. FIG. 11 and FIG. 12 are schematic flowcharts for explaining the acquisition process of oxygen consumption data of the patient P and oxygen consumption data of the oxygenator 2.

First, in ST21 in FIG. 11, an "oxygen saturation and oxygen partial pressure information acquiring unit (program) 51" in FIG. 6 operates to refer to the timing device 24 in FIG. 3, the venous-side oxygen saturation measuring unit 16, the arterial-side oxygen saturation measuring unit 19, the venous-side oxygen partial pressure measuring unit 15, and the arterial-side oxygen partial pressure measuring unit 18 and store measurement data of each measuring unit of each clock time in an "oxygen saturation and oxygen partial pressure information storing unit 52" in FIG. 6.

FIG. 13 is a schematic explanatory diagram showing each piece of measurement data stored in the "oxygen saturation and oxygen partial pressure information storing unit 52." As shown in FIG. 13, "saturation of venous oxygen (%)" data measured by the venous-side oxygen saturation measuring unit 16, "saturation of arterial oxygen (%)" data measured by the arterial-side oxygen saturation measuring unit 19, "partial pressure of venous oxygen (mmHg)" data measured by the venous-side oxygen partial pressure measuring unit 15, and "partial pressure of arterial oxygen (mmHg)" data measured by the arterial-side oxygen partial pressure measuring unit 18, which are associated with measurement clock time data, are stored.

These pieces of data of the saturation of arterial oxygen (%) and the partial pressure of arterial oxygen (mmHg) are examples of "first state information." The pieces of data of the saturation of venous oxygen (%) and the partial pressure of venous oxygen (mmHg) are examples of "second state information."

Subsequently, in ST22, with reference to the timing device 24, whether or not a predetermined time has elapsed is determined. This is to ensure the time of acquisition of data of past saturation of arterial oxygen (%) and so forth in preparation for the case in which the extracorporeal circulation system 1 has not yet acquired the data.

Subsequently, the acquisition process proceeds to ST23. In ST23, a "past data presence/absence check processing unit (program) 53" in FIG. 6 operates to refer to the "final in-body bloodstream passing time storing unit 42" and the "oxygenator bloodstream passing time storing unit 46" in FIG. 5 and determine whether or not the oxygen saturation data and the oxygen partial pressure data of the clock times earlier than the present clock time by "0.36 minute" and by "0.065 minute" are stored in the "oxygen saturation and oxygen partial pressure information storing unit 52."

Specifically, it is determined whether or not pieces of data of the saturation of arterial oxygen (%), the partial pressure of arterial oxygen (mmHg), and so forth associated with the clock time earlier than the present clock time "(8) 12:03:37.00" in FIG. 13 by "0.36 minute" have been stored. Furthermore, it is also determined whether or not pieces of data of the saturation of venous oxygen (%), the partial pressure of venous oxygen (mmHg), and so forth associated with the clock time earlier than the present clock time by "0.065 minute" have been stored.

In the present embodiment, as shown in FIG. 13, pieces of data of the saturation of arterial oxygen (%), the partial pressure of arterial oxygen (mmHg), and so forth associated with "(2) 12:03:01.00," which is the clock time earlier than the present clock time "(8) 12:03:37.00" by "0.36 minute," are stored. Furthermore, pieces of data of the saturation of venous oxygen (%), the partial pressure of venous oxygen (mmHg), and so forth associated with "(5) 12:03:36.35," which is the clock time earlier than the present clock time "(8) 12:03:37.00" by "0.065 minute," are stored.

Therefore, in the present embodiment, it is determined to be true that "pieces of previous data are stored" in ST24 and the acquisition process proceeds to ST25. In ST25, a "first present clock time biological information extraction processing unit (program) 54" in FIG. 6 operates to refer to the timing device 24 and the oxygen saturation and oxygen partial pressure information storing unit 52 and store the values of the saturation of venous oxygen (%) and the partial pressure of venous oxygen (mmHg) of the present clock time in a "first present clock time biological information storing unit 55" in FIG. 6. Specifically, "72%" as the saturation of venous oxygen (%) of clock time "(8) 12:03:37.00" in FIG. 13 and "40 mmHg" as the partial pressure of venous oxygen (mmHg) are stored in the "first present clock time biological information storing unit 55."

Subsequently, the acquisition process proceeds to ST26. In ST26, a "first past clock time biological information extraction processing unit (program) 56" in FIG. 6 operates and refers to the timing device 24, the oxygen saturation and oxygen partial pressure information storing unit 52, and the final in-body bloodstream passing time storing unit 42 in FIG. 5. Then, the "first past clock time biological information extraction processing unit (program) 56" stores the values of the saturation of arterial oxygen (%) and the partial pressure of arterial oxygen (mmHg) of the clock time earlier than the present clock time by the final in-body bloodstream passing time (0.36 minute) in a "first past clock time biological information storing unit 61" in FIG. 7. Specifically, "97%" as the saturation of arterial oxygen (%) of clock time "(2) 12:03:01.00" in FIG. 13 and "132 mmHg" as the partial pressure of arterial oxygen (mmHg) are stored in the "first past clock time biological information storing unit 61" in FIG. 7.

Subsequently, the acquisition process proceeds to ST27. In ST27, an "oxygen consumption calculation processing unit (program) 62" in FIG. 7 operates and refers to the first past clock time biological information storing unit 61 in FIG. 7, the first present clock time biological information storing unit 55, the hemoglobin measuring unit 17, and the flow rate sensor 14. Furthermore, the "oxygen consumption calculation processing unit (program) 62" refers to an "oxygen consumption calculation expression storing unit 63" in FIG. 7. In this oxygen consumption calculation expression storing unit 63, the following expression by which the oxygen consumption of the patient P can be correctly calculated is stored. Specifically, the expression is "(saturation of arterial oxygen of past clock time−saturation of venous oxygen of present clock time)×1.34 (mL/g)×Hgb (g/dL)×Q (d/L (flow rate))+0.003 (mL/mmHg/dL)×(partial pressure of arterial oxygen of past clock time−partial pressure of venous oxygen of present clock time)×Q (d/L (flow rate))." In this expression, 1.34 (mL/g) represents the oxygen volume per 1 mg of Hgb.

Therefore, in ST27, the referenced pieces of data are substituted into these expressions to calculate the oxygen consumption. Furthermore, this obtained oxygen consumption is stored in an "oxygen consumption information storing unit 64" in FIG. 7 with clock time information. The data of the oxygen consumption is generated in this manner. In this expression, the venous blood measured at the present clock time corresponds to the past arterial blood before passing in the body of the patient P. Thus, the correct oxygen consumption can be obtained by making a comparison with the past arterial blood defined in consideration of the time of passing in the body of the patient P (final in-body bloodstream passing time).

Note that in the present embodiment, data of the oxygen saturation and the oxygen partial pressure is used in order to obtain the oxygen consumption of the patient P. However, the present invention is not limited thereto and the oxygen consumption may be obtained with only oxygen saturation or oxygen partial pressure data.

Next, a process of obtaining the oxygen delivery of the oxygenator 2 in FIG. 1 will be described. First, in ST28, a "second present clock time biological information extraction processing unit (program) 65" in FIG. 7 operates to refer to the timing device 24 and the oxygen saturation and oxygen partial pressure information storing unit 52 in FIG. 6 and store the values of the saturation of arterial oxygen (%) and the partial pressure of arterial oxygen (mmHg) of the present clock time in a "second present clock time biological information storing unit 66."

Specifically, "98%" as the saturation of arterial oxygen (%) of clock time "(8) 12:03:37.00" in FIG. 13 and "132 mmHg" as the partial pressure of arterial oxygen (mmHg) are stored in the "second present clock time biological information storing unit 66."

Subsequently, the process proceeds to ST29. In ST29, a "second past clock time biological information extraction processing unit (program) 71" in FIG. 8 operates and refers to the timing device 24, the oxygen saturation and oxygen partial pressure information storing unit 52 in FIG. 6, and the oxygenator bloodstream passing time storing unit 46 in FIG. 5. Then, the "second past clock time biological information extraction processing unit (program) 71" stores the values of the saturation of venous oxygen (%) and the partial pressure of venous oxygen (mmHg) of the clock time earlier than the present clock time by the oxygenator bloodstream passing time (for example, 0.065 minute) in a "second past clock time biological information storing unit 72" in FIG. 8.

Figure 8:
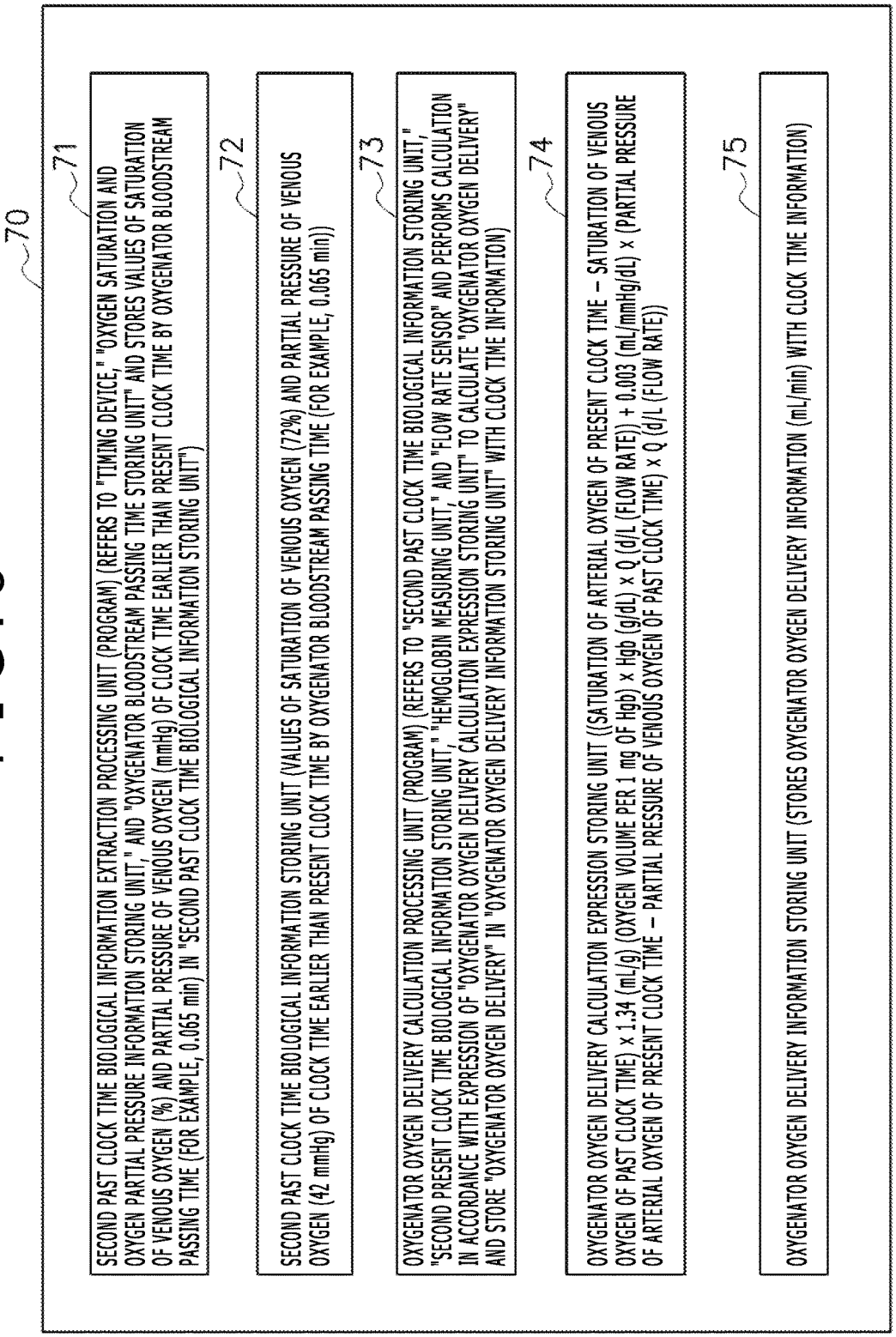
FIG. 8 is a schematic block diagram showing the main configuration of a fifth various-kinds-of-information storing unit.

Specifically, "72%" as the saturation of venous oxygen (%) of clock time "(5) 12:03:36.35" in FIG. 13 and "42 mmHg" as the partial pressure of venous oxygen (mmHg) are stored in the "second past clock time biological information storing unit 72" in FIG. 8.

Subsequently, the process proceeds to ST30. In ST30, an "oxygenator oxygen delivery calculation processing unit (program) 73" in FIG. 8 operates and refers to the second past clock time biological information storing unit 72 in FIG. 8, the second present clock time biological information storing unit 66 in FIG. 7, the hemoglobin measuring unit 17, and the flow rate sensor 14. Furthermore, the "oxygenator oxygen delivery calculation processing unit (program) 73" refers to an "oxygenator oxygen delivery calculation expression storing unit 74" in FIG. 8. In this oxygenator oxygen delivery calculation expression storing unit 74, the following expression by which the oxygen delivery of the oxygenator 2 can be calculated is stored. Specifically, the expression is "(saturation of arterial oxygen of present clock time−saturation of venous oxygen of past clock time)×1.34 (mL/g)×Hgb (g/dL)×Q (d/L (flow rate))+0.003 (mL/mmHg/ dL)×(partial pressure of arterial oxygen of present clock time−partial pressure of venous oxygen of past clock time)×Q (d/L (flow rate))."

Therefore, in ST30, the referenced pieces of data are substituted into these expressions to calculate the oxygenator oxygen delivery. Furthermore, this obtained oxygenator oxygen consumption is stored in an "oxygenator oxygen delivery information storing unit 75" in FIG. 8 with clock time information.

The data of the oxygenator oxygen delivery is generated in this manner. In this expression, the arterial blood measured at the present clock time corresponds to the past venous blood before passing in the oxygenator 2. Thus, the correct oxygen delivery can be obtained by making a comparison with the past venous blood defined in consideration of the time of passing in the oxygenator 2 (oxygenator bloodstream passing time).

Note that in the present embodiment, data of the oxygen saturation and the oxygen partial pressure is used in order to obtain the oxygen delivery of the oxygenator 2. However, the present invention is not limited thereto and the oxygen consumption may be obtained with only oxygen saturation or oxygen partial pressure data.

Furthermore, the present embodiment has a configuration in which the oxygen consumption (mL/minute) of the patient P and the oxygen delivery (mL/minute) of the oxygenator 2 are discriminated and are separately calculated based on different pieces of basic data and so forth. Regarding this point, conventionally both are obtained by a similar calculation expression or the like. Thus, when a measurement value of a blood gas in a tube of the extracorporeal circulation system 1 changes, it is difficult to determine whether this change is attributed to the occurrence of change in the oxygen delivery due to the clogging of the oxygenator 2 or is attributed to the occurrence of change in the oxygen consumption due to change in the state of the patient P. However, in the present embodiment, the oxygen consumption of the patient P and the oxygen delivery of the oxygenator 2 are calculated with discrimination. Thus, differently from the conventional configuration, when a change occurs in a blood gas measurement value, whether this change is clogging of the oxygenator 2 or is change in the state of the patient P can be clearly determined.

Specifically, in the extracorporeal circulation system 1 of the present embodiment, the oxygen consumption of the patient P and the oxygen delivery are separately acquired. Thus, when an abnormality exists in a numerical value or the like of either one of them, which of them is abnormal can be rapidly identified.

This point will be described in detail below by using FIG. 14. FIG. 14 is a schematic explanatory diagram showing the relationship between the oxygen consumption and the oxygen delivery in association with a rise in the body temperature. The example of FIG. 14 is an example in which the body temperature of the patient P rises at clock time "(1) 12:02:37.00" in FIG. 14 and thereafter the oxygen consumption increases and the influence thereof appears in the "saturation of venous oxygen (%)" at "(7) . . . " and "(8) 12:03:37.00."

Specifically, in FIG. 13, because a rise in the body temperature does not occur in the patient P, the "saturation of venous oxygen (%)" at clock times (7) and (8) is "71%" and "72%." However, in FIG. 14, due to the rise in the body temperature, the oxygen consumption increases and the "saturation of venous oxygen (%)" at clock times (7) and (8) is "65%" and "63%." Therefore, when the saturation of arterial oxygen (%) at clock time (2) and the saturation of venous oxygen (%) at clock time (8) are compared in measuring the oxygen consumption of the patient P as described above, the oxygen consumption increases in the case of FIG. 14.

On the other hand, regarding the oxygen delivery of the oxygenator 2, the configuration in which past saturation (i.e., the previous determination corresponding to the "passing time") of venous oxygen (%) and present saturation of arterial oxygen (%) are compared is employed in the present embodiment. Furthermore, the oxygen delivery of the oxygenator 2 is constant from the capability of the oxygenator 2. For this reason, although, at clock times (7) and (8) in FIG. 14, the saturation of venous oxygen (%) decreases from "71%" and "72%" to "65%" and "63%," respectively, compared with FIG. 13, the oxygenator 2 merely adds a certain amount of oxygen to the blood with this numerical value. Therefore, when the oxygen delivery of the oxygenator 2 is measured, the difference between the present saturation of arterial oxygen (%) and the past saturation of venous oxygen (%) does not change.

When this point is shown by FIG. 13 and FIG. 14, the past saturation of venous oxygen (%) at clock time (5) in FIG. 13 is "72%" and the saturation of arterial oxygen (%) of the present (clock time (8)) is "98%" and the difference is "26." On the other hand, the past saturation of venous oxygen (%) at clock time (7), at which the oxygen consumption has increased, in FIG. 14 is "65%" and the saturation of arterial oxygen (%) at clock time (9) after addition of oxygen thereto by the oxygenator 2 is "91%" and the difference is "26." This is because the capability of the oxygenator 2 is "26."

As above, in the present embodiment, when a change occurs in a blood gas due to a state change of the patient P, a body temperature rise, it can be clearly determined that the change is due to the state change of the patient P.

Furthermore, in the present embodiment, determination is carried out by using the latest value of the flow rate sensor 14. However, the present invention is not limited thereto and an average value in a certain period may be used.

Second Embodiment

Figure 16:
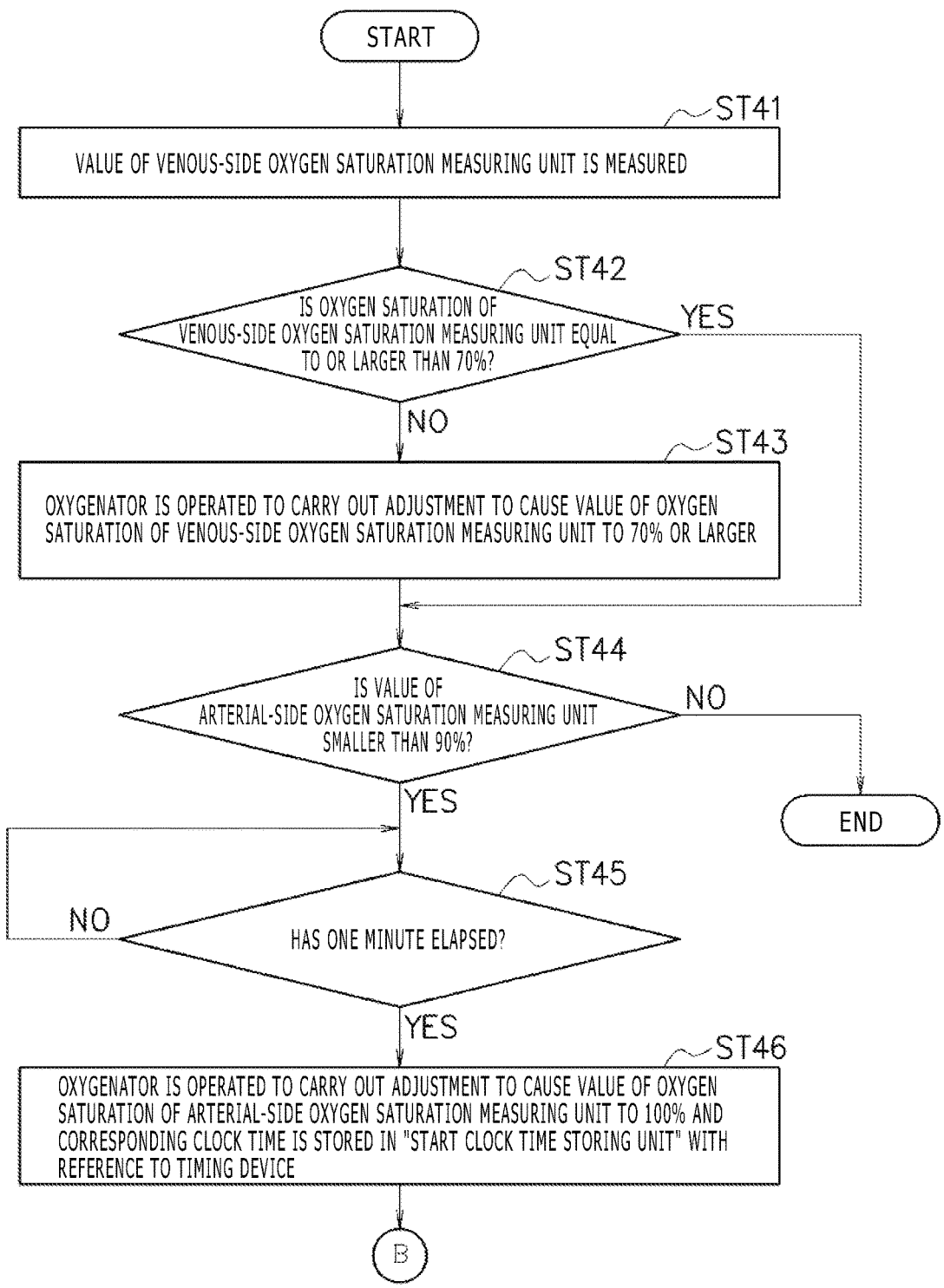
FIG. 16 is a schematic flowchart showing main operation and so forth of the extracorporeal circulation device according to the second embodiment of the present invention.
Figure 17:
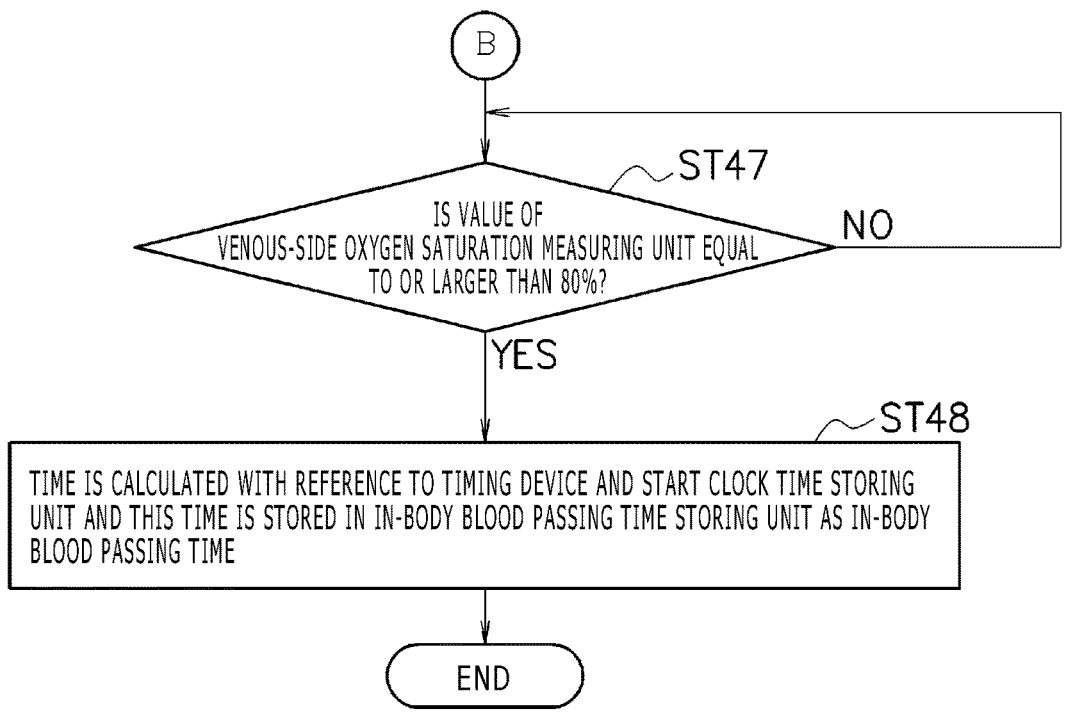
FIG. 17 is another schematic flowchart showing the main operation and so forth of the extracorporeal circulation device according to the second embodiment of the present invention.

FIG. 15 is a schematic block diagram showing the main configuration of an extracorporeal circulation device according to a second embodiment of the present invention. Furthermore, FIG. 16 and FIG. 17 are schematic flowcharts showing main operation and so forth of the extracorporeal circulation device according to the second embodiment of the present invention. Many configurations and steps in the present embodiment are the same as those in the above-described first embodiment. Thus, the common configuration is given the same symbol or the like and description thereof is omitted and description will be made below mainly about differences. In the above-described first embodiment, the time of passing of blood in the body of the patient P is defined from the body weight of the patient P, the flow rate of blood, and so forth before pieces of data of the saturation of arterial oxygen (%) and so forth are acquired. Regarding this point, in the present embodiment, the time of passing of blood in the body of the patient P is not defined from the body weight of the patient P, the flow rate of blood, and so forth. Instead, the time of passing of blood in the body is defined by actually acquiring pieces of data of the saturation of arterial oxygen (%) and so forth from the patient P.

Description will be specifically made below. The contents of the block diagram in FIG. 15 are configurations added in place of configurations in the first embodiment, such as the "basic in-body bloodstream passing time calculating unit (program) 31," the "basic in-body bloodstream passing time calculation expression storing unit 32," the "basic in-body bloodstream passing time storing unit 35," the "basic in-body bloodstream passing time correction processing unit (program) 36," the "basic in-body bloodstream passing time correction base information storing unit 41," and the "final in-body bloodstream passing time storing unit 42." Characteristics of the present embodiment will be described along the flowchart of FIG. 16. FIG. 16 is a schematic flowchart showing an in-body bloodstream passing time calculation process.

First, in ST41 in FIG. 16, a "venous-side oxygen saturation adjusting unit (program) 81" in FIG. 15 operates and measures the value of the venous-side oxygen saturation measuring unit 16 in FIG. 1. Subsequently, the calculation process proceeds to ST42. In ST42, whether or not the value of the oxygen saturation is equal to or larger than 70% is determined. If the value of the oxygen saturation is not equal to or larger than 70% in ST42, the calculation process proceeds to ST43, where the oxygenator 2 is operated to adjust the value of the venous-side oxygen saturation measuring unit 16 to 70% or larger.

Subsequently, the calculation process proceeds to ST44. In ST44, an "arterial-side oxygen saturation adjusting unit (program) 82" in FIG. 15 operates and determines whether the value of the arterial-side oxygen saturation measuring unit 19 in FIG. 1 is smaller than 90%. When the value of the arterial-side oxygen saturation measuring unit 19 is smaller than 90% in ST44, the calculation process proceeds to ST45. In ST45, the "arterial-side oxygen saturation adjusting unit (program) 82" refers to the timing device 24 and waits for one minute.

Subsequently, the calculation process proceeds to ST46. In ST46, an "arterial-side oxygen saturation adjusting unit (program) 83" in FIG. 15 operates to operate the oxygenator 2 to set the value of the arterial-side oxygen saturation measuring unit 19 in FIG. 1 to 100% and store the corresponding clock time in a "start clock time storing unit 84" with reference to the timing device 24.

Subsequently, the calculation process proceeds to ST47. In ST47, an "in-body blood passing time information generating unit (program) 85" in FIG. 15 operates and determines whether or not the value of the venous-side oxygen saturation measuring unit 16 in FIG. 1 has become equal to or larger than 80%. When the value of the venous-side oxygen saturation measuring unit 16 has become equal to or larger than 80% in ST47, the time is calculated with reference to the timing device 24 and the start clock time storing unit 84 and this time is stored in an "in-body blood passing time storing unit 86" in FIG. 15 as, e.g., an "in-body blood passing time" that is in-body passing time information.

As described above, according to the present embodiment, the in-body blood passing time of the patient P is identified based on change in the value of the actual saturation of venous oxygen (%) and therefore the correct in-body blood passing time can be set regarding each patient P. Thus, the oxygen consumption of each patient P can be correctly grasped.

Incidentally, the present invention is not limited to the above-described embodiments.

What is claimed is:

1. An extracorporeal circulation management device comprising:

first controller means programmed for determining a plurality of first oxygenation-related parameter values of blood supplied from an output of an oxygenator unit that carries out gas exchange of blood to a target person with time-course information and for determining a plurality of second oxygenation-related parameter values of blood introduced from the target person into an input of the oxygenator unit with time-course information;

calculation means programmed for determining in-body passing time information defining a time period for blood supplied from the output of the oxygenator unit to the target person to be discharged from the target person according to a bloodstream volume of the target person and a flow rate of the supplied blood; and second controller means programmed for selecting first oxygenation-related parameter values separated by the stored in-body passing time information and for selecting second oxygenation-related parameter values separated by the calculated in-body passing time information as comparison targets to evaluate oxygenation consumption of the target person;

wherein the calculation means is further programmed to correct the in-body passing time information according to locations on the target person where the blood is introduced from the oxygenator unit into the target person and where the blood is discharged from the target person.

2. The extracorporeal circulation management device according to claim 1
wherein the calculation means is further programmed for generating the in-body passing time information based on detected change of the first oxygenation-related parameter values and the second oxygenation-related parameter values.

3. The extracorporeal circulation management device of claim 1 further comprising:
third controller means programmed for determining oxygenator unit passing time information defining a time period for blood supplied from the target person to the input of the oxygenator unit to be discharged from the output of the oxygenator unit; and
fourth controller means programmed for selecting first oxygenation-related parameter values separated by the oxygenator unit passing time information and for selecting second oxygenation-related parameter values separated by the oxygenator unit passing time information as comparison targets to evaluate oxygenation delivery of the oxygenation unit.

4. The extracorporeal circulation management device according to claim 3 further comprising:
fifth controller means programmed for detecting an abnormality of either the oxygenation consumption of the target person or the oxygenation delivery of the oxygenation unit; and
sixth controller means programmed for identifying which of the oxygenation delivery or the oxygenation consumption is abnormal in response to a measured temperature and expected oxygenation consumption at the measured temperature.

5. The extracorporeal circulation management device according to claim 1 wherein the first and second oxygenation-related parameters are comprised of saturation of oxygen and partial pressure of oxygen.

6. An extracorporeal circulation system, comprising:
an oxygenator unit;
a first tube part for providing blood from an output of the oxygenator unit to a target person;
a second tube part for providing blood from the target person to an input of the oxygenator unit;

first oxygenation sensors measuring first oxygenation-related parameters values in the first tube part;
second oxygenation sensors measuring second oxygenation-related parameters values in the second tube part; and
an extracorporeal circulation management device comprising first controller means programmed for determining in-body passing time information defining a time period for blood supplied from the output of the oxygenator unit to the target person to be discharged from the target person according to a bloodstream volume of the target person and a flow rate of the supplied blood, and second controller means programmed for selecting first oxygenation-related parameter values separated by the determined in-body passing time information and for selecting second oxygenation-related parameter values separated by the determined in-body passing time information as comparison targets to evaluate oxygenation consumption of the target person, wherein the in-body passing time information is corrected according to locations on the target person where the blood is introduced from the oxygenator unit into the target person and where the blood is discharged from the target person.

7. The extracorporeal circulation management system according to claim 6, wherein the extracorporeal circulation management device further comprises:
third controller means programmed for generating the in-body passing time information based on detected change of the first oxygenation-related parameter values and the second oxygenation-related parameter values.

8. The extracorporeal circulation management system of claim 6 wherein the extracorporeal circulation management device further comprises:
fourth controller means programmed for determining oxygenator unit passing time information defining a time period for blood supplied from the target person to the input of the oxygenator unit to be discharged from the output of the oxygenator unit; and
fifth controller means programmed for selecting first oxygenation-related parameter values separated by the oxygenator unit passing time information and for selecting second oxygenation-related parameter values separated by the oxygenator unit passing time information as comparison targets to evaluate oxygenation delivery of the oxygenation unit.

9. The extracorporeal circulation management system according to claim 8, wherein the extracorporeal circulation management device further comprises:
sixth controller means programmed for detecting an abnormality of either the oxygenation consumption of the target person or the oxygenation delivery of the oxygenation unit; and
seventh controller means programmed for identifying which of the oxygenation delivery or the oxygenation consumption is abnormal in response to a measured temperature and expected oxygenation consumption at the measured temperature.

10. The extracorporeal circulation management system according to claim 6 wherein the first and second oxygenation-related parameters are comprised of saturation of oxygen and partial pressure of oxygen.

11. A method of managing extracorporeal circulation in a target patient using an oxygenation unit, the method comprising the steps of:
determining a plurality of first oxygenation-related parameter values of blood supplied from an output of the oxygenator unit that carries out gas exchange of blood to the target person with time-course information;
determining a plurality of second oxygenation-related parameter values of blood introduced from the target person into an input of the oxygenator unit with time-course information;
determining in-body passing time information defining a time period for blood supplied from the output of the oxygenator unit to the target person to be discharged from the target person according to a bloodstream volume of the target person and a flow rate of the supplied blood;
selecting first oxygenation-related parameter values separated by the determined in-body passing time information and for selecting second oxygenation-related parameter values separated by the determined in-body passing time information as comparison targets to evaluate oxygenation consumption of the target person; and
correcting the in-body passing time information according to locations on the target person where the blood is introduced from the oxygenator unit into the target person and where the blood is discharged from the target person.

12. The method of claim 11, further comprising the step of:
generating the in-body passing time information based on detected change of the first oxygenation-related parameter values and the second oxygenation-related parameter values.

13. The method of claim 11 further comprising the steps of:
determining oxygenator unit passing time information defining a time period for blood supplied from the target person to the input of the oxygenator unit to be discharged from the output of the oxygenator unit;
selecting first oxygenation-related parameter values separated by the oxygenator unit passing time information and selecting second oxygenation-related parameter values separated by the oxygenator unit passing time information as comparison targets to evaluate oxygenation delivery of the oxygenation unit.

14. The method of claim 13 further comprising the steps of:
detecting an abnormality of either the oxygenation consumption of the target person or the oxygenation delivery of the oxygenation unit; and
identifying which of the oxygenation delivery or the oxygenation consumption is abnormal in response to a measured temperature and expected oxygenation consumption at the measured temperature.

15. The method of claim 11 wherein the first and second oxygenation-related parameters are comprised of saturation of oxygen and partial pressure of oxygen.

* * * * *